United States Patent [19]

Waters, IV et al.

[11] Patent Number: 4,592,348
[45] Date of Patent: Jun. 3, 1986

[54] AEROSOL INHALER

[76] Inventors: William C. Waters, IV, 1255 Kingsley Cir., Atlanta, Ga. 30324; Charles I. Wilmer, 922 Dean Dr., Atlanta, Ga. 30328

[21] Appl. No.: 682,604

[22] Filed: Dec. 17, 1984

[51] Int. Cl.⁴ .......................................... A61M 11/00
[52] U.S. Cl. .............................................. 128/200.23
[58] Field of Search ................ 128/200.23; 222/400.5, 222/402.13

[56] References Cited

U.S. PATENT DOCUMENTS 3,456,646  7/1969  Phillips et al. ................. 128/200.23
3,789,843  2/1974  Armstrong et al. ........... 128/200.23

Primary Examiner—Kyle L. Howell
Assistant Examiner—Daniel Haneiwich
Attorney, Agent, or Firm—Larry A. Roberts

[57] ABSTRACT

An aerosol dispensing device for discharging a metered amount of medication-containing aerosol into the mouth of a patient by manual compression thereof, which effectively times the release of the medication containing aerosol to coincide with the onset of inhalation of the patient to more effectively introduce the medication deeply into the patient's lungs.

8 Claims, 3 Drawing Figures

AEROSOL INHALER

TECHNICAL FIELD

This invention relates generally to an aerosol inhaler used to dispense a measured amount of medication-containing aerosol, and relates more specifically to an aerosol inhaler for timing the release of the medication-containing aerosol to coincide with the inhalation of the user and more efficiently introduce the medication deeply into the lungs of the user.

BACKGROUND OF THE INVENTION

Aerosolized bronchodilator therapy, wherein a measured amount of medication-containing aerosol is inhaled by an asthmatic patient, is considered the mainstay of therapy for asthma. A long-standing problem of this type of treatment is the proper timing of the release of the bronchodilator medication with respect to the onset of inspiration. If an asthma patient receives most of the aerosolized medication at the onset of inspiration, the medication can be carried deeply into the lungs and thus constitute more effective therapy. In contrast, if the aerosolized medication is dispensed too early or too late with respect to the onset of inspiration, the medication will be sprayed ineffectively into the mouth, or may be inhaled only shallowly, so that the medication is expelled without ever reaching the lungs when the patient exhales. This problem becomes even more apparent when considered in the context of a severe asthma attack, for as bronchoconstriction worsens, the patient's ability to inspire becomes progressively more limited. With such a severely limited airflow, the asthma patient must receive the bronchodilator medication at the very onset of inspiration, or else the limited amount of air able to reach the patient's lungs will not carry the essential medication.

Other inhalers known to the art have not successfully confronted this problem, and, as will be seen, allow a patient to spray the medicine into his mouth out of synchronization with inhalation. For example, U.S. Pat. No. 3,456,646 discloses an aerosol inhaler which comprises a housing, a air passage within the housing, a vane disposed in one end of the air passage, a mouthpiece disposed at the other end of the air passage, and an aerosol container being reciprocally received in said housing, disposed so as to inject a metered amount of medication-containing aerosol into the air passage. In this apparatus, a mechanical linkage activated by the vane prevents the aerosol container from discharging its medication into the air passage so long as the vane is in its normal "closed" position. The user places his mouth on the mouthpiece and inhales, creating a pressure differential which causes the vane to pivot, displacing the mechanism linkage and thereby permitting the aerosol container to reciprocate into the housing and to inject its measured amount of medication into the air passage.

U.S. Pat. No. 3,732,864 discloses another aerosol inhaler which discharges its medicine during the patient's inhalation, the inhalation serving to release a gate which normally blocks actuation of the device. This apparatus is similar to that disclosed in the '646 patent, but with the mechanical linkage eliminated and the gate disposed directly underneath the aerosol container. When the user inhales on the mouthpiece, the gate, which normally restrains the aerosol container in its fully extended attitude, rotates out of the way, thereby permitting the container to reciprocate into the housing and dispense its measured amount of medication.

Both of these prior art inhalers require a predetermined minimum airflow during inhalation before medication can be discharged into the housing for inspiration by the user. Additionally, neither of these prior art inhalers synchronizes the release of the medication with the onset of inhalation, and the inhalers thus are often ineffective in delivering the medicine deep into the lungs. Moreover, since these devices require a certain minimal vacuum and airflow in order to operate the valve mechanism, a severely distressed patient may not be able to generate sufficient suction to operate the inhaler, thereby precluding the very therapy so desperately needed. In addition, if a user is uncertain whether he has succeeded in properly inhaling the medication into his lungs, he may be disposed to discharge the device more than once, which could lead to a dangerous overdosage of the medication.

SUMMARY OF THE INVENTION

As will be seen, the invention disclosed herein overcomes these and other problems associated with the conventional aerosol inhaler. Stated in general terms, the aerosol inhaler of the present invention comprises a means for properly timing the release of bronchodilator medication to coincide with the onset of inspiration by the patient. Stated in somewhat greater detail, the present inhaler has an air passage into which medication is introduced from a medication dispenser as the patient inhales air drawn through an air passage. The air passage normally is nearly closed by a valve so that little air enters the passage when the patient begins to inhale. The valve operates in response to the medication dispenser to open the air passage only when medication is dispensed while the patient attempts to inhale, allowing the medication to enter the initial flow of the moving air stream inhaled by the patient.

Stated more specifically, a conventional pressurized aerosol bottle containing bronchodilator medication is mounted reciprocally atop a dispenser housing having an air passage. A mouthpiece is disposed at one end of the air passage, and the other end of the passage constitutes an air inlet. A valve is mounted in the air inlet and is normally held in a closed position by a flange on one end of a lever. Downward pressure on the aerosol bottle applies force against the lever, thereby displacing the flange away from the valve and releasing the valve to rotate freely in response to inhalation by the patient. Thus, as the aerosol bottle is downwardly reciprocated, a metered amount of medication is released into the air passage simultaneous with the sudden rush of air occasioned by the opening of the valve after the patient begins to inhale.

The basic concept of the apparatus is that, instead of the patient having to coordinate breathing and the delivery of the medication into the inhaler, the patient must simply inhale through the device and press the aerosol bottle downwardly, which will simultaneously result in delivering a sudden rush of air and a metered amount of medication into the patient's lungs. The device thereby synchronizes the release of the medication with the very onset of inspiration and thus assures correct dosage and maximal delivery of the medicine in the most efficient manner.

Thus, it is an object of this invention to provide an improved aerosol inhaler for the dispensation of metered amounts of bronchodilator medication.

It is a further object of this invention to provide an aerosol inhaler which provides for the proper timing of the release of the bronchodilator medication to coincide with the onset of inspiration by the patient.

It is another object of this invention to provide an aerosol inhaler which can afford therapy to severely distressed asthmatics who may not be able to generate sufficient vacuum to operate a traditional inhaler.

Another object of this invention is to provide an aerosol inhaler which will reliably deliver medication into the lungs on the first attempt and will thus obviate the necessity for a user to repeat the procedure and risk a possibly dangerous overdosage of the medication.

It is a further object of this invention to provide an inexpensive, durable aerosol inhaler.

Other objects, features, and advantages of the present invention will become apparent upon reading the following specifications when taken in conjunction with the drawing and the appended claims.

DETAILED DESCRIPTION OF THE INVENTION

Figure 1:
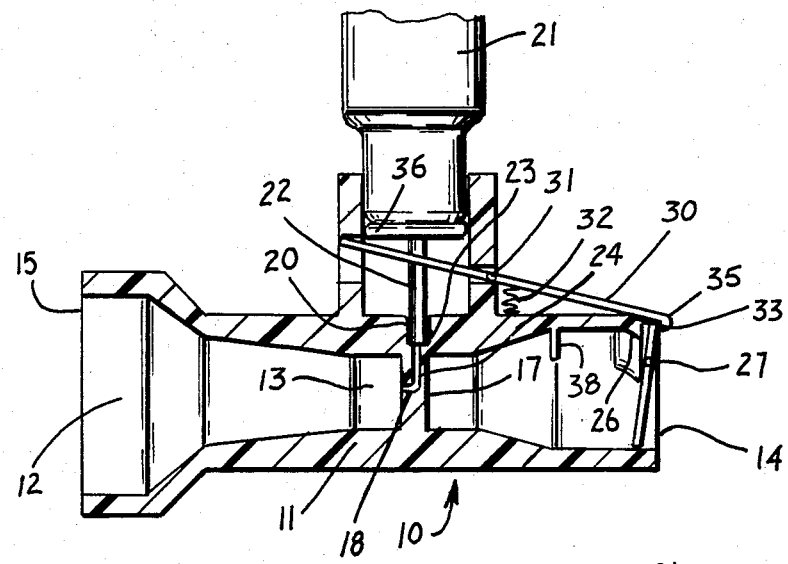
FIG. 1 is a side cross-sectional view of an apparatus according to the disclosed embodiment of the present invention.
Figure 2:
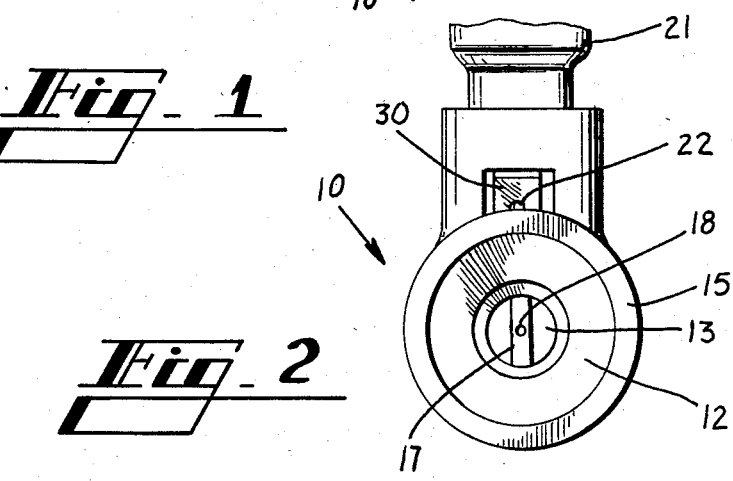
FIG. 2 is an end elevation view of the apparatus in FIG. 1 as seen from one end of the apparatus.
Figure 3:
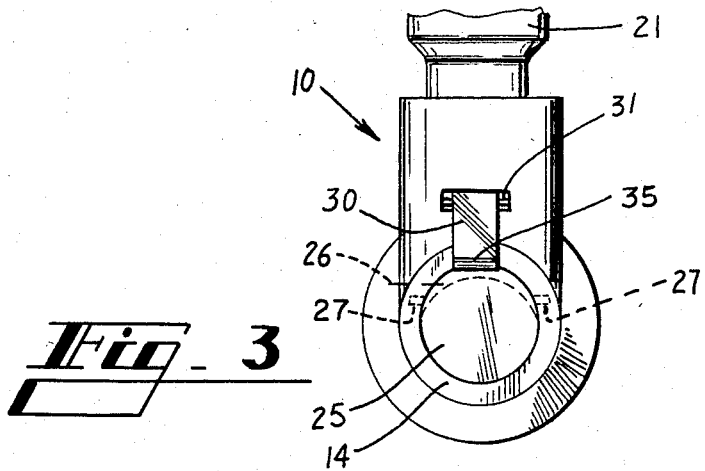
FIG. 3 is an end elevation view of the apparatus in FIG. 1 as seen from the opposite end from that shown in FIG. 2.

Referring now in more detail to the drawing in which like numerals represent like parts throughout the several views, FIG. 1 shows an aerosol inhaler 10 embodying the principles of the present invention. A housing 11 contains an air passage 12 with a venturi throat 13, one end of the air passage 12 defining an air inlet 14, and the other end of the air passage 12 communicative with a mouthpiece 15. A pipe 17 is vertically disposed within the venturi throat 13 perpendicular to the longitudinal axis of the venturi throat and defines dispensing port 18 located along the longitudinal axis of the venturi throat and disposed on the side of the pipe facing the mouthpiece 15.

A port 20 designed to slidably receive an aerosol dispensing bottle 21 is disposed atop the housing 11 concentrically with pipe 17. The aerosol bottle 21 is conventional to the art and includes a hollow spring-loaded valve stem 22 which, when depressed against spring pressure into the top of the aerosol bottle 21, dispenses a metered amount of aerosolized medication. When the aerosol bottle 21 is inserted into the port 20, the valve steam 22 rests against a support member 23 formed by the bottom of the port. Downward reciprocation of the aerosol bottle 21 forces the valve stem 22 against the support member 23 and depresses the valve stem 22 into the aerosol bottle 21 to dispense a metered dosage of medication. A passage 24 defined by support member 23 and disposed within the pipe 17 opens into the air passage 12 at dispensing port 18 to provide for flow of medication from the valve steam 22 into the air passage 12.

A butterfly valve 25 is mounted within the air inlet 14 for rotation about an eccentric axis 27. It will be appreciated by those skilled in the art that if the butterfly valve were mounted about a central axis, the pressure exerted on the valve by the inhalation force of the user would be equal on either side of the central axis, and the butterfly valve would thereby be impeded from rotating open. By providing an eccentric axis, the pressure exerted on the larger portion of the butterfly valve is greater than that exerted on the smaller portion of the valve, thereby expediting the rotation of the valve. It will also be appreciated that the air passage must be shaped to accommodate the rotation of the butterfly valve about an eccentric axis, since the wider portion of the valve would otherwise bind against the wall of the air passage when rotated to open into an air passage of the same size and shape as the valve. In the closed attitude, butterfly valve 25 rests on a valve seat 26 formed in the housing 11 within the air passage 12 so as to let no more than a minimum of air pass around the valve. A lever 30 is pivotably mounted atop the housing 11 by a hinge 31, and a tension spring 32 urges the lever 30 toward a normal position shown in FIG. 1. When the lever 30 is in its normal position, a flange 33 on the end of the lever 30 engages and retains the butterfly valve 25 in its closed attitude against valve seat 26. The lever 30 has an angled end 35 which, when contacted by the butterfly valve 26 upon the valve's return to its normally closed position, urges the lever upwardly, allowing the butterfly valve to pivot past the lever. Downward reciprocation of the aerosol bottle 21 applies a downward force against the lever 30 at a contact point 36, causing the lever 30 to pivot about its hinge 31 and disengaging the flange 33 from the butterfly valve 25. As the butterfly valve pivots open, stop 38 disposed in the air passage 12 prevents the butterfly valve from rotating past a horizontal position.

To use the apparatus, a user places his lips around the mouthpiece 15 and begins to inhale. The butterfly valve 25 within the air inlet 14 at the opposite end of the air passage 12 is held closed by the flange 33 on the end of the lever 31, and the design of the butterfly valve permits only a small amount of air to leak around the closed valve so that the user must exert negative pressure inside the air passage with his lungs and will be less tempted to use only his mouth muscles as one would in sucking liquids through a straw. As the user exerts this negative pressure with his lungs, he pushes on the aerosol bottle 21 relative to the bottom of the housing 11, reciprocating the aerosol bottle into the housing. This downward reciprocation depresses the valve stem 22 into the aerosol bottle 21, thereby releasing a metered amount of medication into the venturi throat 13 of the air passage 12. As the downward reciprocation of the aerosol bottle 21 into the housing 11 releases the medication, the bottle simultaneously exerts a force on the lever 30 which pivots the lever counterclockwise (as shown in FIG. 1) and disengages the flange 33 from the butterfly valve 25, permitting the valve to pivot freely. As the butterfly valve 25 is released, the negative pressure inside the air passage 12 occasioned by the user's inhalational force exerted on the mouthpiece 15 causes the butterfly valve to pivot open, allowing a sudden rush of air to flow through the air passage. The reduced air pressure within the venturi passage 13 helps to atomize the liquid droplets of medication entering the air stream moving through the air passage 12 and entrains the medication with the air inhaled into the patient's lungs. Since the user is already exerting inhalational force, this sudden, unrestricted air flow carries the aerosolized medication deep into the user's lungs.

Upon completion of administering the dosage, the user readies the apparatus for the next dosage by rotating the butterfly valve 25 toward the closed position with his finger. As the butterfly valve 25 contacts the angled end 36 of the lever 30, the lever is urged upwardly, allowing the butterfly valve to pivot past the lever to contact the valve seat 26. As the butterfly valve 25 pivots past the angled end 36 of the lever 30, spring 32 urges the lever back toward its normal position where flange 33 engages and retains the butterfly valve in its closed attitude against the valve seat 26.

An optional embodiment of the invention comprises a one-way expiratory valve to enable the user to keep his mouth around the mouthpiece pending a second dosage. Such a one-way valve is normally operative to cover vent slots in the housing communicative with the air passage, and selectively operative to uncover the slots. Thus, the user cannot inhale air through the one-way vent during the inhalation process, but can expel air through the vent, thereby retaining the mouthpiece of the device in his mouth pending a second dosage.

Another optional embodiment comprises an electrical or mechanical timer to indicate to the user how long the inhaled breath should be held before expiration. The timer is started by the reciprocation of the aerosol bottle into the housing. The user inhales the aerosolized medication and holds the inhaled breath until a predetermined time has expired, at which time the timer will indicate to the user, by a light-emitting diode or other appropriate signal, that exhalation is appropriate.

Finally, it will be understood that the preferred embodiment of the present invention has been disclosed by way of example and that other modifications may occur to those skilled in the art without departing from the scope and spirit of the appended claims.

What is claimed is:

1. An aerosol inhaler device for dispensing a metered amount of medication, including a housing, an air passage defined by said housing, an air inlet in communication with one end of said air passage, a mouthpiece in communication with the other end of said air passage through which a user inhales, and a means selectively actuated for dispensing a metered amount of aerosolized medication into said air passage, wherein the improvement comprises:

a valve disposed in said air passage and normally operative to substantially obstruct airflow by user inhalation through said air passage; and means operative in response to actuation of said means for dispensing the aerosolized medication for permitting said valve to open by user inhalation, whereby unobstructed airflow through said air passage to said mouthpiece in response to inhalation by the user is permitted only in response to dispensinag the medication into said air passage.

2. An aerosol inhaler device as recited in claim 1, wherein said air passage comprises a venturi-shaped throat disposed to receive the dispensed medication.

3. An aerosol inhaler device for use with a container adapted to dispense a metered amount of aerosolized medication, comprising:

a housing;

means defining an air passage within said housing;

means associated with said housing for receiving said container to dispense said metered amount of aerosolized medication into said air passage at a predetermined location;

a mouthpiece communicative with one end of said air passage through which a user inhales;

an air inlet communicative with the opposite end of said air passage;

a valve disposed within said air passage and normally operative to substantially obstruct airflow through said air passage when a user inhales through said mouthpiece; and means disposed in operative relation with said container and operative in response to dispensing said aerosolized medication therefrom to permit said valve to open when a user inhales through said mouthpiece, so that unobstructed airflow through said air passage in response to inhalation through said mouthpiece is permitted only in response to dispensing said aerosolized medication into said air passage.

4. An aerosol inhaler device as recited in claim 3, wherein the means for controlling the operation of said valve comprises:

a lever mounted on the housing; and a stop member at one end of said lever, said stop member being normally operative to retain said valve in its closed attitude, and said lever being selectively operative in response to dispensing medication to disengage said stop member from said valve, thereby permitting said valve to open in response to user inhalation.

5. An aerosol inhaler device as recited in claim 4, further comprising bias means urging said lever to a normal position to maintain the stop member, in engaging position with the valve.

6. An aerosol inhaler device as recited in claim 3, wherein said valve is disposed within the air inlet.

7. An aerosol inhaler device as recited in claim 3, further comprising a valve seat molded into said housing and disposed so that the valve rests upon said valve seat when the valve is normally operative.

8. An aerosol inhaler device as recited in claim 3, wherein said air passage further includes a venturi-shaped throat disposed at said predetermined location at which said metered amount of aerosolized medication is dispensed into said air passage.

* * * * *